United States Patent
Tang et al.

Patent Number: 6,040,126
Date of Patent: Mar. 21, 2000

[54] PHOTOGRAPHIC YELLOW DYE-FORMING COUPLERS

[75] Inventors: Ping-Wah Tang, Yorktown; Barbara B. Lussier; Stanley W. Cowan, both of Rochester, all of N.Y.

[73] Assignee: Eastman Kodak Company, Rochester, N.Y.

[21] Appl. No.: 09/218,512

[22] Filed: Dec. 22, 1998

[51] Int. Cl.$^7$ .............................. G03C 1/08; G03C 7/26; G03C 7/32
[52] U.S. Cl. ......................... 430/557; 430/543; 430/556
[58] Field of Search .................................. 430/556, 557, 430/543, 544, 388, 389

[56] References Cited

U.S. PATENT DOCUMENTS

| | | | |
|---|---|---|---|
| 4,336,327 | 6/1982 | Tanaka et al. | 430/556 |
| 4,404,274 | 9/1983 | Curai et al. | 430/389 |
| 5,213,958 | 5/1993 | Motoki et al. | 430/557 |
| 5,427,898 | 6/1995 | Tang et al. | 430/389 |
| 5,677,114 | 10/1997 | Lussier et al. | 430/388 |
| 5,834,167 | 11/1998 | Lussier et al. | 430/557 |

*Primary Examiner*—Geraldine Letscher
*Attorney, Agent, or Firm*—Arthur E. Kluegel

[57] ABSTRACT

A photographic element comprises a light sensitive silver halide emulsion layer having associated therewith an open chain α-carbonyl acetanilide yellow dye-forming coupler having the formula:

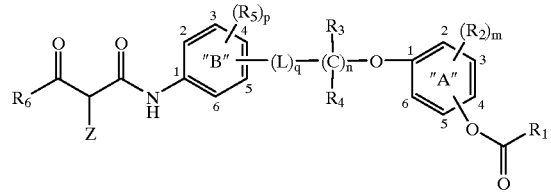

wherein $R_1$ is selected from the group consisting of alkyl, aryl, heterocyclic, and amino groups, provided that $R_1$ may form a ring bonded to another carbon atom which is a member of Ring "A";

each $R_2$ is independently selected from the group consisting of those substituents having a Hammett's sigma value of 0 or less, and m is from 0 to 4;

each $R_3$ and $R_4$ for each of the n carbon atoms is independently selected from the group consisting of hydrogen, alkoxy, aryl, heterocyclic, aryloxy, and alkyl groups, and n is 0 to 16;

each $R_5$ is independently selected from the group consisting of amino, alkyl groups, and groups linked to the "B" ring by oxygen or sulfur, and p is 1 to 3, provided that two $R_5$ groups may join to form a ring;

$R_6$ is selected from the group consisting of alkyl, aryl, and amino groups;

each L is independently a divalent linking group and q is 0 to 3; and

Ring "A" is bonded indirectly to the 3-, 4-, or 5-position of Ring "B"; and

Z is hydrogen, or a group capable of coupling-off when the coupler reacts with an oxidized color developing agent.

11 Claims, No Drawings

PHOTOGRAPHIC YELLOW DYE-FORMING COUPLERS

FIELD OF THE INVENTION

The present invention relates to novel α-carbonyl acetanilide compounds that are useful as photographic couplers and form yellow dyes having improved stability against fading when exposed to light. The invention further relates to a color photographic element containing such novel coupler compounds.

BACKGROUND OF THE INVENTION

Coupler compounds that form yellow image dyes upon coupling with the oxidation products of p-phenylenediamine color developing agents are described in such patents and literature as U.S. Pat. Nos. 2,298,443, 2,407,210, 2,287,057, 3,048,194, 3,265,506, 3,447,928, 4,022,620, and 4,443,536; and "Farbkupplereine Literature Ubersicht" published in Agfa Mitteilungen, Band III, pp. 112–126 (1961). The ability of the yellow image dye to resist light fading is important to the longevity of the color image, especially those images that are exposed to light over long periods of time, such as professional portraits.

U.S. Pat. No. 5,677,114 discloses improved stability to light fading of the yellow image dye by incorporating a ballast group comprising a stabilizing group in the yellow dye-forming coupler. Still further improvement in the resistance to fading of yellow dyes is desired for modem color photographic papers.

Therefore, a problem to be solved is to provide a dye-forming coupler capable of forming, upon coupling with the oxidation product of a p-phenylenediamine color developer, a yellow image dye having improved resistance to fading after prolonged and constant exposure to light. The need for such a coupler is especially great for use in photographic color paper for forming reflection prints of excellent light fading stability.

SUMMARY OF THE INVENTION

The compounds of the invention are of the formula:

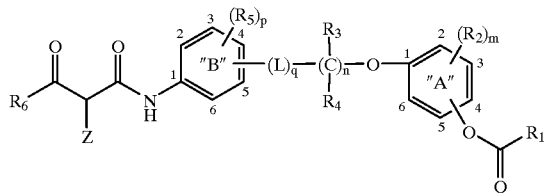

wherein
  $R_1$ is selected from the group consisting of alkyl, aryl, heterocyclic, and amino groups, provided that $R_1$ may form a ring bonded to another carbon atom which is a member of Ring "A";
  each $R_2$ is independently selected from the group consisting of those substituents having a Hammett's sigma value of 0 or less, and m is from 0 to 4;
  each $R_3$ and $R_4$ for each of the n carbon atoms is independently selected from the group consisting of hydrogen, alkoxy, aryl, heterocyclic, aryloxy, and alkyl groups, and n is 0 to 16;
  each $R_5$ is independently selected from the group consisting of amino, alkyl groups, and groups linked to the "B" ring by oxygen or sulfur, and p is 1 to 3, provided that two $R_5$ groups may join to form a ring;
  $R_6$ is a multicarbocyclic or multiheterocyclic group having a tertiary carbon atom as a common vertex through which it is attached to the indicated carbonyl group of the compound;
  each L is independently a divalent linking group and q is 0 to 3;
  Ring "A" is bonded indirectly to the 3-, 4-, or 5-position of Ring "B", and
  Z is hydrogen, or a group capable of coupling-off when the coupler reacts with an oxidized color developer.

The invention further provides a novel photographic element, especially a color photographic paper, comprising a light sensitive silver halide emulsion layer containing a compound of the invention as a yellow dye-forming coupler. The resulting yellow dyes have outstanding light stability.

DETAILED DESCRIPTION OF THE INVENTION

The compounds of the invention, as shown in Formula (I) above, comprise a novel and unobvious combination of structural components. The combination includes a multicyclic substituent $R_6$, preferably an adamantyl group, and a ballast group that has a stabilizing functional group attached thereto. This novel structural combination provides a coupler compound that reacts with p-phenylene diamine developing agents to form photographic yellow image dyes of unexpectedly good light stability, which is highly desirable in photographic color paper reflection prints.

$R_1$, the substituent attached to the acyloxy group on the ring "A", may be an alkyl, aryl, heterocyclic, or an amino group. Also, $R_1$ may form a ring bonded to another carbon atom which is a member of Ring "A". Particularly suitable are alkyl (including cycloalkyl and branched alkyl), amino, fused alkyl, and aryl groups, especially methyl, isopropyl, fused alkyl, t-butyl, dimethylamino, diethylamino, phenyl, and fused amino.

Each $R_2$ is a substituent on the phenoxy ring "A", and there may be up to four of these substituents. $R_2$ is selected from substituents having a Hammett's sigma value of 0 or less. Hammett's sigma values are provided in C. Hansch and A. J. Leo. "Substituent Constants for Correlation Analysis in Chemistry and Biology", Wiley, New York, N.Y., 1979. Values less than 0 indicate that a substituent has an electron donating effect relative to hydrogen. Thus, $R_2$ is electron donating and at least one $R_2$ group is located ortho to the acyloxy group containing $R_1$. Suitably, $R_2$ is an alkyl, alkoxy or amino, including thioalkyl, dialkylamino, and branched alkyl and alkoxy groups. Appropriate examples include t-butyl, t-pentyl, t-octyl, and isopropyl.

When n is greater than 1 the $R_3$ and $R_4$ substituents bonded to each of the n carbon atoms may be independently selected. Besides hydrogen, suitable $R_3$ and $R_4$ substituents include alkyl, alkoxy (including polyalkoxy), aryl, aryloxy, heterocyclic, and amino groups. Alkyl or alkoxy groups of 1–18 carbon atoms and hydrogen are preferred substituents. If desired, $R_3$ or $R_4$ may form a ring with another $R_3$ or $R_4$ group.

$R_5$ is a substituent which may or may not be present as indicated by the subscript "p". Each $R_5$ is a substituent which may be an amino group, an alkyl group, or a group linked to the "B" ring by an atom of oxygen or sulfur. Suitably, one or more of the $R_5$ substituents may occupy the 2-, 4-, or 6-position of the ring "B". Suitably, $R_5$ may be bonded to the ring "B" by an acyloxy, alkylthio, alkyl, amino, or oxy group. Particularly suitable groups are alkylacyloxy, arylacyloxy, trifluoromethyl, alkylthio, alkoxy, aryloxy, alkyl, or amino groups. The value of "p" may range from 0 to 3.

The substituent $R_6$ is a multicyclic group bonded to the rest of the coupler by a carbon atom forming the vertex of two or more rings. Examples of such groups, any of which may be substituted or may contain hetero atoms or unsaturated bonds, include the following:

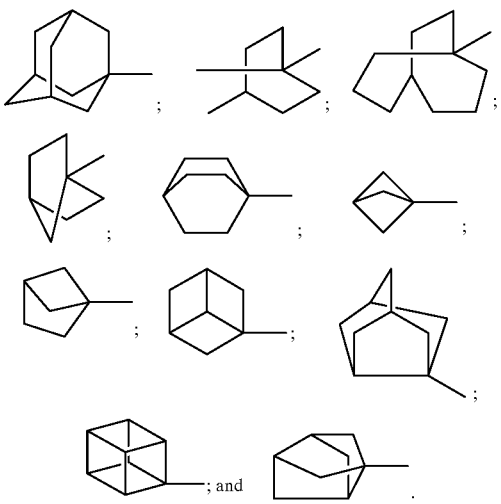

In each of the above illustrated groups, $R_6$, has a common vertex through which it is attached to the indicated carbonyl group of the coupler backbone. Especially preferred as $R_6$ is the adamantyl radical.

In accordance with the present invention, it has been discovered that novel α-carbonyl acetanilide coupler compounds, as depicted in Formula (I), having both a multicarbocyclic or multiheterocyclic substituent $R_6$, preferably, adamantyl, attached to the indicated acyl group and a ballast group having a carbonyloxy-substituted aromatic ring, as in ring "A" of Formula (I), form yellow dyes that have unexpectedly superior resistance to fading when exposed to light over a long period. Such light stability is especially important when the photographic element of the invention is a photographic paper having a reflective support and, more particularly, when the element is a professional portrait paper which is used to form prints that will be exposed to light over long periods of time.

The group L is optionally present. As indicated by the value of q of up to three, there may be as many as three L groups. Each of the L groups may be independently selected to provide a linkage between the ring "B" and the remainder of the coupler. In the broadest sense, L may be any divalent group linking the ballast directly or indirectly with a non-coupling position of the rest of the coupler. Each L may be represented, for example, by one of the groups: —CONR$_7$—, —NR$_7$CO—, —SO$_2$NR$_7$—, —NR$_7$SO$_2$—, —OCO—, —COO—, —R$_8$O—, —O—, —R$_8$OCO— and —R$_8$COO—.

wherein $R_7$ is hydrogen or an alkyl group and $R_8$ is an alkylene group. Especially useful are:

—CONH—, —NHCO—, —O—, —NHSO$_2$—, —OCO— and —COO—.

The group Z represents hydrogen or a coupling-off group which can be split from the coupler upon reaction with oxidized color developer, e.g., p-phenylene diamine. Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, halogen, especially chlorine, alkoxy, aryloxy, heterocyclyl-oxy, sulfonyloxy, acyloxy, acyl, heterocyclyl, sulfonamido, mercaptotetrazole, benzothiazole, mercaptopropionic acid, phosphonyloxy, arylthio, and arylazo. Especially useful coupling-off groups are aryloxy groups and nitrogen-containing heterocyclic groups bonded to the coupling position via a nitrogen atom in the ring. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in UK. Patents and published application Nos. 1,466,728, 1,531, 927, 1,533,039, 2,006,755A and 2,017,704A, the disclosures of which are incorporated herein by reference.

The following examples further illustrate the coupler compounds of the invention.

Y-1

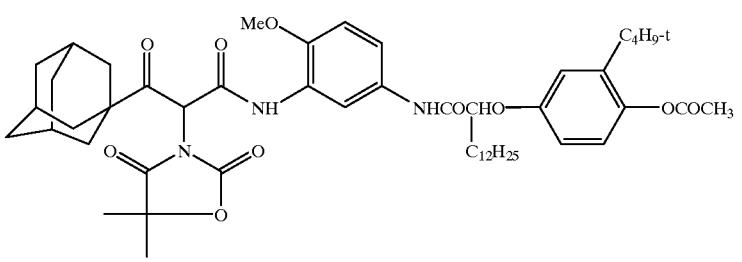

-continued
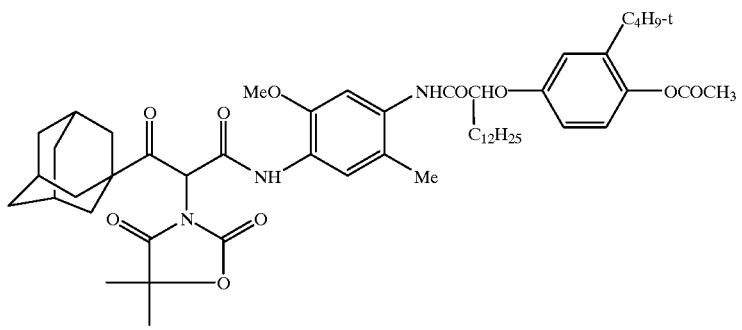
Y-2
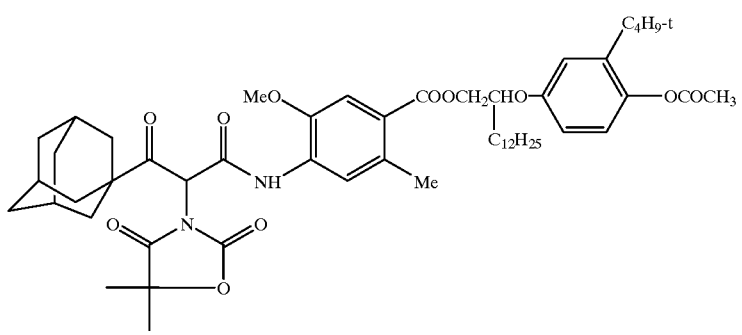
Y-3
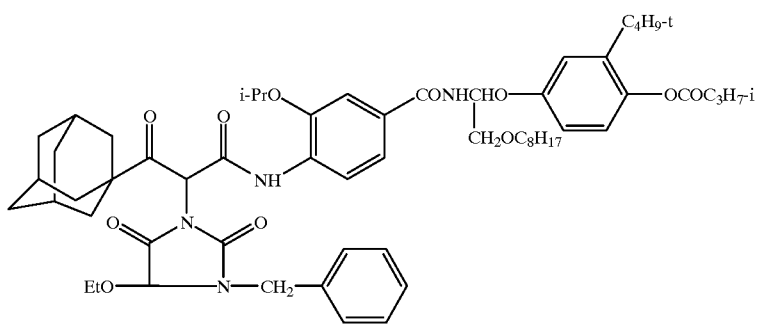
Y-4
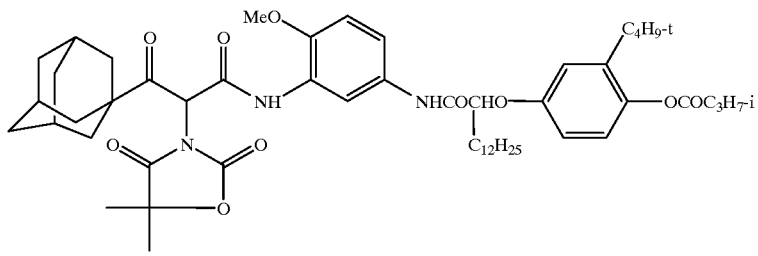
Y-5
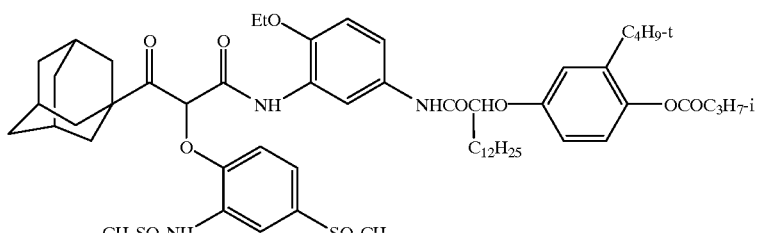
Y-6

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)-hexanamido, alpha-(4-hydroxy-3-t-butylphenoxy)tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

Typically, when employed as photographic dye-forming couplers the compounds of the invention are incorporated in a photographic emulsion melt and coated as a layer described herein on a support to form part of a photographic element. When the term "associated" is employed, it signifies that a reactive compound is in or adjacent to a specified layer where, during processing, it is capable of reacting with other components.

The photographic elements of the invention can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1996, Item 38957, available as described above, which is referred to herein by the term "Research Disclosure". The contents of the Research Disclosure, including the patents and publications referenced therein, are incorporated herein by reference, and the Sections hereafter referred to are Sections of the Research Disclosure.

Except as otherwise specifically provided, the silver halide emulsion-containing elements of the present invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 *Research Disclosure*, Item No. 36544 referenced above, is updated in the September 1996 *Research Disclosure*, Item No. 38957. Certain desirable photographic elements and processing steps, including those useful in conjunction with color reflective prints, are described in *Research Disclosure*, Item 37038, February 1995.

Other image dye-forming couplers may also be included in the photographic element of the invention, including couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323; EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO0257 854; EPO 0284 240; EPO 0 341 204; EPO 347,235; EPO 365,252; EPO 0 422 595; EPO 0 428 899; EPO 0 428 902; EPO 0 459 331; EPO 0 467 327; EPO 0 476 949; EPO 0 487 081; EPO 0 489 333; EPO 0 512 304; EPO 0 155 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912,265; and German OLS 40 08 067. Typically such couplers are pyrazolones, pyrazoloazoles, or pyrazolobenzimidazoles that form magenta dyes upon reaction with oxidized color developing agents.

In addition to the couplers of the invention, photographic elements of the invention can also contain other couplers that form yellow dyes upon reaction with oxidized color developing agent such as those described in such representative patents and publications as: "Farbkuppler-eine Literature Ubersicht," published in Agfa Mitteilungen; Band III; pp. 112–126 (1961); as well as U.S. Pat. Nos. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474; 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632,345; 3,928,041; 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminiphenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. Nos. 4,301,235; 4,853, 319 and 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983, 608; 4,070,191; and 4,273,861; German Applications DE 2,706,117 and DE 2,643,965; UK. Patent 1,530,272; and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Usually the couplers are dispersed in a high-boiling organic solvent in a weight ratio of solvent to coupler of 0.1 to 10.0 and typically 0.1 to 2.0 although dispersions using no permanent coupler solvent are sometimes employed.

The invention materials may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. Nos. 4,163, 669; 4,865,956; and 4,923,784, may be useful. Also contemplated is use of the compositions in association with nucleating agents, development accelerators or their precursors (UK Patent 2,097,140; UK. Patent 2,131,188); electron transfer agents (U.S. Pat. Nos. 4,859,578; 4,912,025); anti-fogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543,323.) Also, the compositions may be blocked or coated in protected form as described, for example, in Japanese Application 61/258,249 or U.S. Pat. No. 5,019,492.

The invention materials may further be used in combination with image-modifying compounds that release PUGS such as "Developer Inhibitor-Releasing" compounds (DIR's). DIR's useful in conjunction with the compositions of the invention are known in the art and examples are described in U.S. Pat. Nos. 3,137,578; 3,148,022; 3,148, 062; 3,227,554; 3,384,657; 3,379,529; 3,615,506; 3,617, 291; 3,620,746; 3,701,783; 3,733,201; 4,049,455; 4,095, 984; 4,126,459; 4,149,886; 4,150,228; 4,211,562; 4,248, 962; 4,259,437; 4,362,878; 4,409,323; 4,477,563; 4,782, 012; 4,962,018; 4,500,634; 4,579,816; 4,607,004; 4,618, 571; 4,678,739; 4,746,600; 4,746,601; 4,791,049; 4,857, 447; 4,865,959; 4,880,342; 4,886,736; 4,937,179; 4,946, 767; 4,948,716; 4,952,485; 4,956,269; 4,959,299; 4,966, 835; 4,985,336 as well as in patent publications GB 1,560, 240; GB 2,007,662; GB 2,032,914; GB 2,099,167; DE 2,842,063, DE 2,937,127; DE 3,636,824; DE 3,644,416 as well as the following European Patent Publications: 272, 573; 335,319; 336,411; 346, 899; 362, 870; 365,252; 365, 346; 373,382; 376,212; 377,463; 378,236; 384,670; 396, 486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

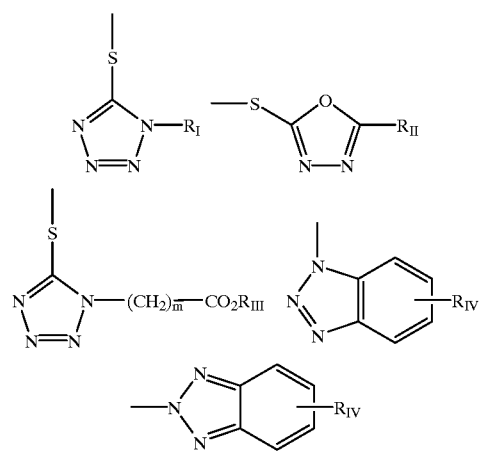

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and $-SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, $-COOR_V$ and $-NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. Nos. 4,438,193; 4,618,571) and groups that combine the features described above. It is typical that the timing group is of one of the formulas:

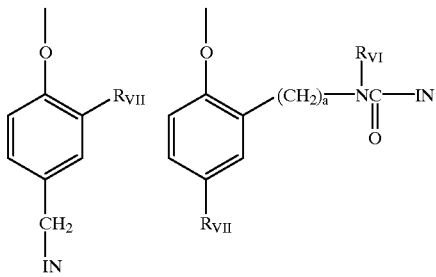

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

The coupler compounds of the present invention are especially useful for obtaining reflection color prints as described in Research Disclosure, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. Nos. 4,346,165; 4,540,653 and 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072, 634; 90-077,822; 90-078,229; 90-078,230; 90-079,336; 90-079,337; 90-079,338; 90-079,690; 90-079,691; 90-080, 487; 90-080,488; 90-080,489; 90-080,490; 90-080,491; 90-080,492; 90-080,494; 90-085,928; 90-086,669; 90-086, 670; 90-087,360; 90-087,361; 90-087,362; 90-087,363; 90-087,364; 90-088,097; 90-093,662; 90-093,663; 90-093, 664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by Research Disclosure, Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of the total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435, 501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061, 609, Tsaur et al U.S. Pat. Nos. 5,147,771, '772, '773,5,171, 659 and 5,252,453, Black et al U.S. Pat. Nos. 5,219,720 and 5,334,495, Delton U.S. Pat. Nos. 5,310,644, 5,372,927 and 5,460,934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat.

No. 4,414,306, Maskasky U.S. Pat. Nos. 4,400,463, 4,713,323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271,858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320,938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye. If desired "Redox Amplification" as described in Research Disclosure XVIIIB(5) may be used.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emulsions coated on a transparent support and may be processed, for example, in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3'15" or less and desirably 90 or even 60 seconds or less.

The photographic element of the invention can be incorporated into exposure structures intended for repeated use or exposure structures intended for limited use, variously referred to by names such as "single use cameras", "lens with film", or "photosensitive material package units".

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The element is sold with instructions to process using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

Preferred color developing agents are p-phenylenediamines such as:

4-amino-N,N-diethylaniline hydrochloride,
4-amino-3-methyl-N,N-diethylaniline hydrochloride,
4-amino-3-methyl-N-ethyl-N-(2-methanesulfonamidoethyl) aniline sesquisulfate hydrate,
4-amino-3-methyl-N-ethyl-N-(2-hydroxyethyl)aniline sulfate,
4-amino-3-(2-methanesulfonamidoethyl)-N,N-diethylaniline hydrochloride, and
4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The entire contents of the patents and other publications referred to in this specification are incorporated herein by reference.

Coupler Synthesis

The following synthetic example illustrates the preparation of coupler Y-1 of this invention. Other couplers of the invention can be prepared by the same general procedure.

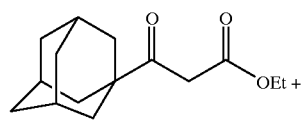

[1]

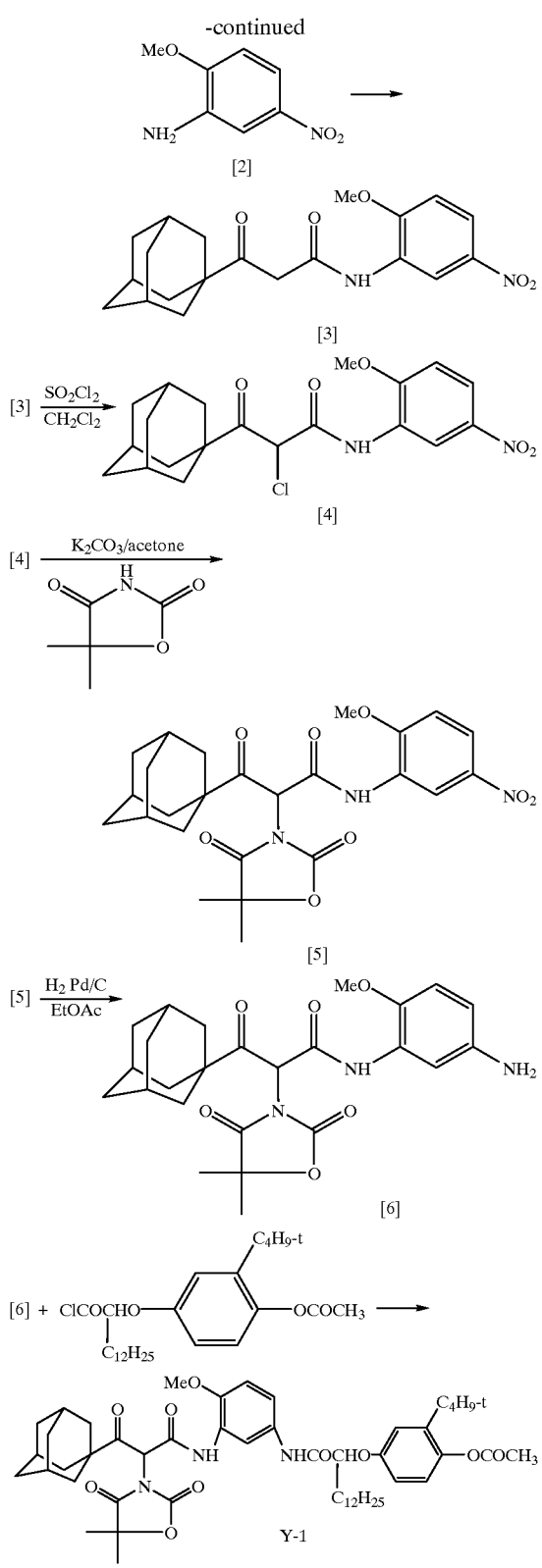

Preparation of 2-[3-(1-adamantyl)-3-oxopropanamido]-4-nitroanisole [3]

Ethyl 3-(1-adamantyl)-3-oxopropionate (57.58 g, 0.23 mol), 2-methoxy-5-nitroaniline (33.63 g, 0.20 mol), and 300 mL toluene were heated at reflux for 16 hours while the byproduct ethanol was distilled off. The mixture was cooled to ca. 50° C. and the reaction mixture was concentrated in vacuo to ca. 50 mL. The mixture was then poured into 2 liters of ligroin with vigorous stirring. The solid was collected, washed with ligroin, and dried in vacuo to yield 62 g (83%) of white solid. All analytical data confirmed the assigned structure.

Preparation of 2-[3-(1-adamantyl)-2-chloro-3-oxopropanamido]-4-nitroanisole [4]

To a suspension of 29.80 g (0.080 mol) of [3] in 250 mL $CH_2Cl_2$ was added 6.75 mL (11.34 g, 0.084 mol) of sulfuryl chloride. The mixture was gently refluxed for 1 hour, followed by stirring at room temperature for 0.5 hour. The solvent was removed in vacuo to yield an oil which solidified upon standing. It was washed with pentane and dried to yield 29.82 g (91.6%) of the desired product.

Preparation of 2-[3-(1-adamantyl)-2-(5,5-dimethyl-2,4-dioxooxazolidinyl)-3-oxopropanamido]-4-nitroanisole [5]

A suspension of 16.28 g (0.04 mol) of [4], 5.17 g (0.04 mol) of 5,5-dimethyloxazolidine-2,4-dione, and 16.58 g (0.12 mol) of anhydrous potassium carbonate in 380 mL of dried acetone was refluxed for 3 hours. Thin layer chromatographic analysis indicated that the reaction was complete. The reaction mixture was concentrated in vacuo to yield an orange-colored solid. It was dissolved in ethyl acetate and the organic layer was washed with HCl (10%) and brine until neutrality. The organic layer was dried, filtered, and concentrated to yield an oil which solidified upon standing. It was triturated in ligroin. The final dried product (15.92 g, 79.8%) gave one spot on TLC. All analytical data confirmed the assigned structure.

Preparation of 2-[3-(1-adamantyl)-2-(5,5-dimethyl-2,4-dioxooxazolidinyl)-3-oxopropanamido]-4-aminoanisole [6]

The nitro compound [5] was reduced in ethyl acetate using a catalytic amount of Pd/C under 42 p.s.i. of hydrogen. The amine was used in situ in the following step.

Preparation of Coupler Y-1

To a solution of 3.02 g (6.82 mmol) of [6] and 0.94 g (7.7 mmol) of N,N-dimethylaniline in 50 mL of ethyl acetate, stirred at room temperature under $N_2$, was added the acid chloride prepared from 3.34 g (7.69 mmol) of 2-(4-acetoxy-3-tert-butylphenoxy)tetradecanoic acid, in ethyl acetate. The reaction mixture was stirred for 3 hours. The mixture was worked up in aqueous acid. The ethyl acetate layer was dried over $MgSO_4$, filtered, and the solvent was removed in vacuo. The isolated product was purified by flash column chromatography on silica gel, using a solvent gradient to 35% ethyl acetate in ligroin to yield 3.2 g (64%) of the desired product, Coupler Y-1. All analytical data confirmed the assigned structure.

Preparation of Photographic Elements

The photographic elements of Examples 1–9 containing the couplers shown in Table 1 were prepared as follows:

On a gel-subbed, polyethylene-coated paper support were coated the following layers:

First Layer

An underlayer containing 3.23 grams gelatin per square meter.

Second Layer

A photosensitive layer containing (per square meter) 2.15 grams gelatin, an amount of blue-sensitized silver chloride emulsion containing 0.28 grams silver; a dispersion containing (8.80×10$^{-4}$ mole) of coupler, and 0.043 gram surfactant Alkanol XC (trademark of E. I. Dupont Co.) (in addition to the Alkanol XC used to prepare the coupler dispersion). The coupler dispersion contained the coupler, all of the gelatin in the layer except that supplied by the emulsion, an amount of dibutyl phthalate equal to 46.5% of the weight of coupler, an amount of 2-[2-(butoxyethoxy) ethyl acetate equal to 38.7% of the weight of coupler, and 0.22 gram Alkanol XC.

Third Layer

A protective layer containing (per square meter) 1.40 grams gelatin, 0.15 gram bis(vinylsulfonyl)methyl ether, 0.043 gram Alkanol XC, and $4.40 \times 10^{-6}$ gram tetraethylammonium perfluorooctanesulfonate.

A series of comparative coupler compounds, C-1 through C-6, were prepared for comparison with the coupler compounds of the invention. Structural formulae of the comparative compounds are as follows:

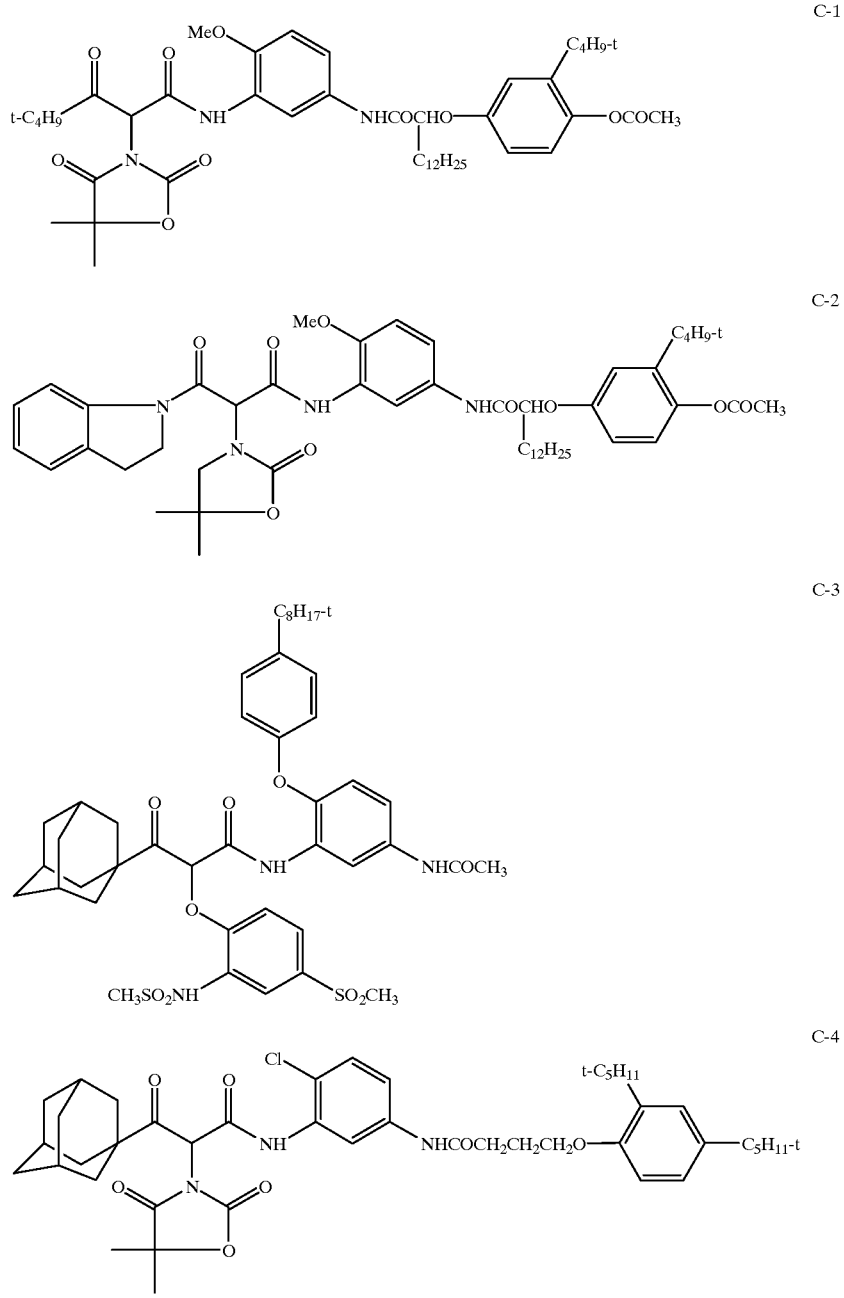

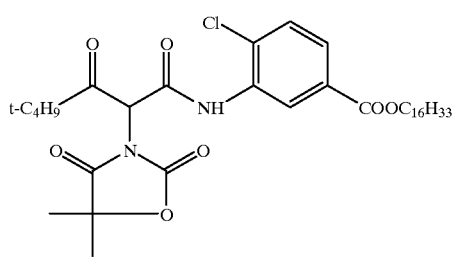

C-5

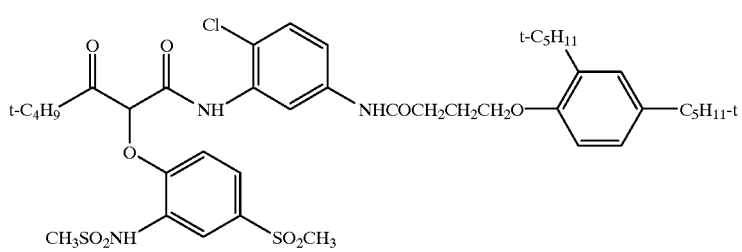

C-6

None of the comparative couplers have the novel combination of substituents that characterize the couplers of the invention, such substituents including a multicyclic group ($R_6$) and a carbonyloxy substituent on a phenoxy group connected (preferably through a linking group) to a phenyl ring of the coupler ballast. Prior art references relevant to one or more of the comparative couplers include U.S. Pat. No. 5,677,114 (Ex. Y-2); U.S. Pat. Nos. 5,213,958; 5,427,898 (Ex. Y-1); U.S. Pat. Nos. 4,336,327 and 4,404,274.

Photographic elements containing either a coupler of the invention or a comparative coupler were prepared as described above and tested as described hereinafter.

Preparation of Processed Photographic Examples

Processed samples were prepared by exposing the coatings through a step wedge and processing as follows:

| Process Step | Time (min.) | Temp. (C.) |
|---|---|---|
| Developer | 0.75 | 35.0 |
| Bleach-Fix | 0.75 | 35.0 |
| Water wash | 1.50 | 35.0 |

The processing solutions used in the above process had the following compositions (amounts per liter of solution):

| Developer | |
|---|---|
| Triethanolamine | 12.41 g |
| Blankophor REU (trademark of Mobay Corp.) | 2.30 g |
| Lithium polystyrene sulfonate | 0.09 g |
| N,N-Diethylhydroxylamine | 4.59 g |
| Lithium sulfate | 2.70 g |
| Developing agent Dev-1 | 5.00 g |
| 1-Hydroxyethyl-1,1-diphosphonic acid | 0.49 g |
| Potassium carbonate, anhydrous | 21.16 g |
| Potassium chloride | 1.60 g |
| Potassium bromide | 7.00 mg |
| pH adjusted to 10.4 at 26.7 C. | |
| Bleach-Fix | |
| Solution of ammonium thiosulfate | 71.85 g |
| Ammonium sulfite | 5.10 g |
| Sodium metabisulfite | 10.00 g |
| Acetic acid | 10.20 g |
| Ammonium ferric ethylenediaminetetra acetate | 48.58 g |
| Ethylenediaminetetraacetic acid | 3.86 g |
| pH adjusted to 6.7 at 26.7 C. | |

Dev-1

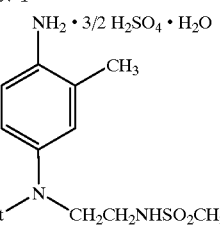

The density of each step of each strip was measured. The strips were then covered by UV-absorbing filters (in lieu of coating a similar filter layer over the photosensitive layer of the photographic element) and subjected to irradiation by the light of a xenon arc lamp at an intensity of 5,400 lux for a total of 36 weeks, the densities being measured periodically during the test as indicated in Table 2. The light stability of the dye ("Stab"), expressed as the density to green light remaining from an initial density of 1.0, is shown in Table 1.

TABLE 1

| | Elapsed Time of Irradiation | | | | |
|---|---|---|---|---|---|
| Coupler | 6 wks | 12 wks | 18 wks | 24 wks | 36 wks |
| Y-1 | 1.00 | 0.99 | 0.97 | 0.94 | 0.91 |
| C-1 | 0.99 | 0.99 | 0.96 | 0.84 | 0.80 |
| C-2 | 0.89 | 0.74 | 0.60 | 0.47 | 0.33 |
| C-3 | 0.98 | 0.92 | 0.86 | 0.77 | 0.65 |
| C-4 | 0.99 | 0.96 | 0.90 | 0.86 | 0.77 |
| C-5 | 0.91 | 0.74 | 0.52 | 0.35 | 0.23 |
| C-6 | 0.99 | 0.92 | 0.79 | 0.61 | 0.42 |

The results shown in the above table indicate an unexpected improvement in light stability for the yellow dye produced by the coupler of the invention which has as substituents both a muticyclic group on the acyl portion of the molecule and a ballast having a stablizing group on the acetanilide portion. The comparative compounds, each of which contained one or the other but not both of said groups, formed yellow dyes having markedly less stability to long term exposure to light.

This invention has been described in detail with particular reference to certain preferred embodiments thereof, but it will be understood that variations and modifications can be effected within the spirit and scope of the invention.

What is claimed is:

1. A photographic element comprising a light sensitive silver halide emulsion layer having associated therewith an open chain a-carbonyl acetanilide yellow dye-forming coupler compound having the formula:

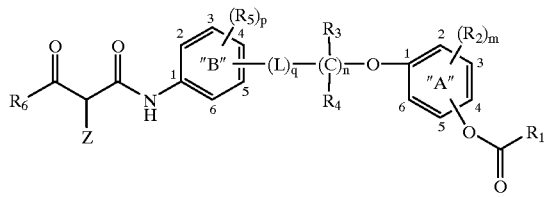

wherein $R_1$ is selected from the group consisting of alkyl, aryl, heterocyclic, and amino groups, provided that $R_1$ may form a ring bonded to another carbon atom which is a member of Ring "A";

each $R_2$ is independently a substituent having a Hammett's sigma value of 0 or less, and m is from 0 to 4;

each $R_3$ and $R_4$ for each of the n carbon atoms is independently selected from the group consisting of hydrogen, alkoxy, aryl, heterocyclic, aryloxy, and alkyl groups, and n is 0 to 16;

each $R_5$ is independently selected from the group consisting of amino, alkyl groups, and groups linked to the "B" ring by oxygen or sulfur, and p is 1 to 3, provided that two $R_5$ groups may join to form a ring;

$R_6$ is a multicarbocyclic or multiheterocyclic group having a common vertex through which it is attached to the indicated carbonyl group;

each L is independently a divalent linking group and q is 0 to 3;

Ring "A" is bonded indirectly to the 3-, 4-, or 5-position of Ring "B", and

Z is hydrogen or a group capable of coupling-off when the coupler reacts with an oxidized color developer.

2. The element of claim 1 wherein Z is aryloxy or a nitrogen-containing heterocyclic group bonded to the coupling position the coupler compound through a nitrogen atom in the ring.

3. The element of claim 2 wherein Z additionally contains an oxygen atom in the nitrogen-containing heterocyclic group.

4. The element of claim 1 wherein m is at least 1.

5. The element of claim 1 wherein each of l, m, n and p is 1.

6. The element of claim 5 wherein at least one $R_2$ substituent on ring "A" is ortho to the acyloxy group to which $R_1$ is attached.

7. The element of claim 6 wherein at least one $R_2$ substituent is a branched alkyl group.

8. The element of claim 6 wherein said at least one $R_2$ substituent is i-propyl, t-butyl, t-amyl, or t-octyl.

9. The element of claim 1 wherein $R_1$ has at least 4 carbon atoms.

10. The element of claim 1 wherein at least one $R_5$ is bonded at the 2-,4-, or 6-position of ring "B".

11. The element of claim 1 wherein q is at least 1 and each L is —CONH—, —NHCO—, —O—, —NHSO$_2$—, —OCO— or —COO—, wherein R is hydrogen or an alkyl group and R' is an alkylene group.

* * * * *